United States Patent [19]

McArthur et al.

[11] Patent Number: 5,426,090

[45] Date of Patent: Jun. 20, 1995

[54] HETEROCYCLIC COMPOUNDS

[75] Inventors: Alastair McArthur, Rotterdam/Pernis, Netherlands; Trevor W. Newton, Sittingbourne, England

[73] Assignee: Shell Research Limited, United Kingdom

[21] Appl. No.: 90,668

[22] Filed: Jul. 12, 1993

Related U.S. Application Data

[63] Continuation-in-part of Ser. No. 616,591, Nov. 21, 1990, abandoned.

[51] Int. Cl.[6] ............................................. A01N 43/54
[52] U.S. Cl. ..................................... 504/243; 504/242; 544/302; 544/318
[58] Field of Search ................ 544/302, 318; 504/242, 504/243

[56]   References Cited

U.S. PATENT DOCUMENTS 4,973,354  11/1990  Hatanaka et al. ................... 544/302

*Primary Examiner*—John M. Ford

[57]   ABSTRACT

A method of combating undesired plant growth in wheat, comprising treating said undesired plant growth with an effective amount of a compound of the formula I

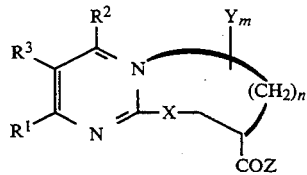

in which
n is an integer from 1 to 6;
m is an integer from 0 to $2n+2$;
X represents an oxygen or sulphur atom or a sulphinyl or sulphonyl group;
$R^1$, $R^2$ and $R^3$ each independently represents a hydrogen or halogen atom, a formyl, cyano, carboxy or azido group, or an optionally substituted $C_{1-12}$ alkyl, $C_{2-12}$ alkenyl, $C_{2-12}$ alkynyl, $C_{1-12}$ alkoxy, $C_{2-12}$ alkenyloxy, $C_{2-12}$ alkynyloxy, $C_{1-12}$ alkylthio, $C_{2-12}$ alkenylthio, $C_{2-12}$ alkynylthio, $C_{1-12}$ alkylcarbonyl, $C_{1-12}$ alkoxycarbonyl, amino, aminoxy or di-$C_{1-12}$ alkyliminoxy group;
Z represents a hydrogen or halogen atom, a hydroxy group, an optionally substituted $C_{1-12}$ alkoxy, $C_{2-12}$ alkenyloxy, $C_{2-12}$ alkynyloxy, ($C_{3-8}$ cycloalkyl)oxy, phenyloxy, $C_{1-12}$ alkylthio, $C_{2-12}$ alkenylthio, $C_{2-12}$ alkynylthio, phenylthio, sulphonamido, aminoxy or di-$C_{1-12}$ alkyliminoxy group; and
Y represents a halogen atom, a cyano or carboxy group, or an optionally substituted $C_{1-12}$ alkyl, $C_{2-12}$ alkenyl, $C_{2-12}$ alkynyl, $C_{1-12}$ alkoxy, $C_{2-12}$ alkenyloxy, $C_{2-12}$ alkynyloxy, $C_{1-12}$ alkylthio, $C_{2-12}$ alkenylthio, $C_{2-12}$ alkynylthio, phenyloxy, $C_{1-12}$ alkylcarbonyl or $C_{1-12}$ alkoxycarbonyl group;
or a carboxylic acid salt of a compound of formula I with an equivalent amount of an inorganic or organic cation.

20 Claims, No Drawings

HETEROCYCLIC COMPOUNDS

This application is a continuation-in-part application of U.S. patent application Ser. No. 07/616,591, filed Nov. 21, 1990, now abandoned.

The present invention relates to certain heterocyclic compounds, their preparation and their use as herbicides.

A number of 2-substituted pyrimidine compounds are known to have plant growth regulant or herbicidal properties.

Certain 2-alkyl/alkenyl/aralkyl/aryl-oxy pyrimidine compounds are described in East German Patent Specification No. 109170 as useful plant growth regulants, being able to regulate metabolic and growth process, for example promoting root formation and growth, encouraging fruit release and giving rise to dwarf features in plants.

More recently, a series of publications have documented the herbicidal properties of various 2-aryloxy- or 2-arylthio-pyrimidines, see, for example, European Patent Specification Nos. 223,406A and 249,708A and Japanese Patent Specification Nos. 63 258 462 A and 63 258 463 A.

It has now been found that especially useful herbicidal activity is present in pyrimidine derivatives bearing a substituted cycloalkoxy group at the 2-position; compounds which are structurally and sterically very different to the alkyl and aryl oxy/thio pyrimidines of the prior art.

In accordance with the present invention, there is provided a compound of the general formula I

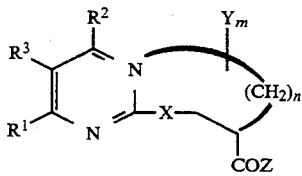

in which
n is an integer from 1 to 6;
m is an integer from 0 to 2n+2;
X represents an oxygen or sulphur atom or a sulphinyl or sulphonyl group;
$R^1$, $R^2$ and $R^3$ each independently represents a hydrogen or halogen atom, a formyl, cyano, carboxy or azido group, or an optionally substituted alkyl, alkenyl, alkynyl, alkoxy, alkenyloxy, alkynyloxy, alkylthio, alkenylthio, alkynylthio, alkylcarbonyl, alkoxycarbonyl, amino, aminoxy or dialkyliminoxy group;
Z represents a hydrogen or halogen atom, a hydroxy group, an optionally substituted alkoxy, alkenyloxy, alkynyloxy, cycloalkoxy, aryloxy, alkylthio, alkenylthio, alkynylthio, arylthio, sulphonamido, aminoxy or dialkyliminoxy group; and
Y represents a halogen atom, a cyano or carboxy group, or an optionally substituted alkyl, alkenyl, alkynyl, alkoxy, alkenyloxy, alkynyloxy, alkylthio, alkenylthio, alkynylthio, aryloxy, alkylcarbonyl or alkoxycarbonyl group; or a carboxylic acid salt of a compound of general formula I with an equivalent amount of an inorganic or organic cation.

An alkyl, alkenyl or alkynyl radical or moiety may be a straight or branched chain group. Generally an alkyl radical or moiety has from 1 to 12 carbon atoms, preferably from 1 to 6, especially from 1 to 4, carbon atoms. Alkenyl and alkynyl radicals or moieties suitably have from 2 to 12 carbon atoms, preferably from 2 to 6, especially from 2 to 4, carbon atoms. Cycloalkyl groups suitably have from 3 to 8 carbon atom ring members.

An aryl radical, or an aryl moiety in an aryloxy or arylthio radical, may be a single or fused carbocyclic ring system having from 6 to 10 ring members. Suitably an aryl radical or moiety comprises a single ring system and preferably is a phenyl ring.

A heterocyclic radical is suitably a single or fused, saturated or unsaturated ring system having from 5 to 10, preferably 5 or 6, ring members of which from 1 to 3 ring members may be hetero atoms selected from oxygen, nitrogen and sulphur atoms.

Certain radicals represented by the symbols $R^1$, $R^2$, $R^3$, Z and Y may be unsubstituted or substituted Where substituents are present, the substituent groups may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds. There may be one or more of the same or different substituents present in each radical.

Optional substituents for alkyl, alkenyl, alkynyl, alkoxy, alkenyloxy, alkynyloxy, alkylthio, alkenylthio, alkynylthio, alkylcarbonyl, alkoxycarbonyl or cycloalkoxy groups may be independently selected from one or more of halogen atoms and alkoxy, alkenyloxy, hydroxy, alkylthio, alkylsulphonyl, alkylsulphinyl, alkylenedioxy, alkylenedithio, haloalkyl and alkoxycarbonyl groups, and dialkyliminoxy, optionally substituted amino, trialkylsilyl, alkylcarbonyl, alkoxycarbonyl, carboxy, cyano, thiocyanato and optional substituted aminocarbonyl groups. For the group Z, optional substituents for the appropriate specified radicals may also be independently selected from aryl, aryloxy, arylthio, arylcarbonyl and heterocyclic groups.

Optional substituents for aryl, aryloxy or arylthio groups or heterocyclic rings may be independently selected from one or more of halogen atoms and nitro, cyano, alkyl, haloalkyl, alkoxy, alkylthio, aryloxy, alkoxycarbonyl and aralkoxycarbonyl groups.

Optional substituents for an amino group or for an amino moiety in an aminoxy or aminocarbonyl group, may suitably be independently selected from alkyl, alkenyl, aryl, alkoxy, amino, mono-or di-alkylamino, arylamino, alkoxyalkyl, haloalkyl, hydroxy, hydroxyalkyl, cyano, carboxyalkyl or alkylcarbonylamino, or the amino group may form part of a heterocyclic ring.

Optional substituents for a sulphonamido group include optionally substituted alkyl, aryl or heterocyclic groups.

An alkyl radical or moiety when present as a substituent or as part of a substituent group, preferably has from 1 to 4 carbon atoms, especially 1 or 2 carbon atoms. A haloalkyl radical suitably has from 1 to 3 halogen atoms and a preferred haloalkyl radical is a trifluoromethyl group. As a substituent an alkenyl or alkynyl moiety suitably has from 2 to 4 carbon atoms. An aryl radical when present as a substituent is preferably a phenyl group. A halogen atom as a substituent is suitably a fluorine, chlorine or bromine atom.

Carboxylic acid salts of the compounds of general formula I include salts with inorganic cations derived from alkali metals, alkaline earth metals such as, for example, sodium, potassium, calcium and magnesium, and transition metals, for example copper, and with organic cations such as alkylammonium and alkylsulphonium cations.

n is preferably 3, 4 or 5 to give a cyclopentyl, cyclohexyl or cycloheptenyl group. It is especially preferred that n is 3 or 4.

Suitable examples of the radicals $R^1$ and $R^2$ include hydrogen atoms, halogen atoms, $C_{1-4}$alkyl groups, $C_{1-4}$alkoxy groups, $C_{1-4}$alkylthio groups, and mono- and di-$C_{1-4}$alkylamino groups. Preferably $R^1$ and $R^2$ are independently selected from chlorine atoms, methyl groups, methoxy groups, methylthio groups, methylamino groups and dimethylamino groups, especially from chlorine atoms, methyl groups and methoxy groups.

Preferably the radical $R^3$ is a hydrogen atom.

X preferably represents an oxygen atom.

Suitable examples of the group Z include hydrogen atoms, hydroxy groups, $C_{1-4}$alkoxy groups, phenoxy groups, benzyloxy group, thienylmethoxy groups, ($C_{1-2}$alkoxy)$C_{1-2}$alkoxy groups, $C_{1-4}$alkylthio groups, phenylthio groups, ($C_{1-2}$alkylthio)$C_{1-2}$alkoxy groups, dimethyliminoxy groups, $C_{1-4}$alkylsulphonamido groups, phenylsulphonamido and benzylsulphonamido groups in which the phenyl ring is unsubstituted or substituted by halogen, carboxy or alkoxycarbonyl, and thienylsulphonamido groups. Preferably the group COZ is a carboxylic acid group or a derivative thereof, especially a carboxy, methoxycarbonyl or ethoxycarbonyl group, or is a sulphonylcarbamoyl group, especially phenylsulphonylcarbamoyl; COZ being a carboxy, methoxycarbonyl or ethoxycarbonyl group is especially preferred.

There may be one or more substituents Y in the cycloalkyl group which may be the same or different substituents selected from, for example, halogen atoms and cyano, nitro, $C_{1-4}$alkyl, halo$C_{1-4}$alkyl, $C_{1-4}$alkoxy, $C_{1-4}$alkylthio, phenoxy, carboxy and ($C_{1-4}$alkoxy)carbonyl groups. Preferably, a substituent Y is selected from chlorine atoms and cyano, nitro, trifluoromethyl, methyl and phenoxy groups. However, it is most preferred that no substituent Y is present, i.e. that m is 0.

It will be appreciated that the compounds of the present invention can exist in a number of different stereoisomeric forms. The compounds have two chiral centres, shown as * and ** in formula (Ia) below;

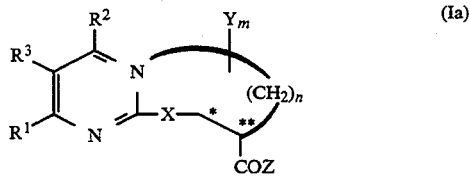

thus there are 2 diastereoisomers, each of which comprises a mixture of 2 enantiomers. The present invention is to be understood to include all individual isomeric forms of the compounds of general formula I and mixtures thereof in whatever proportion. It will be further appreciated that one isomer may have a greater activity than another isomer of the same compound or than a mixture of isomers.

The present invention further provides a process for the preparation of a compound of the present invention, which process comprises reacting a compound of the general formula II

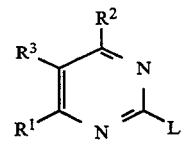

in which $R^1$ $R^2$ and $R^3$ are as defined above and L represents a leaving group, with a compound of the general formula III

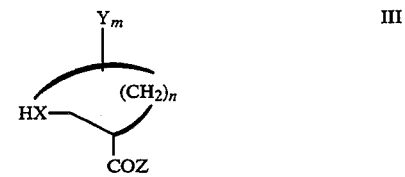

in which n, m, X, Y, and Z are as defined above, and, if required or desired, converting a compound of general formula I into another compound of general formula I, or converting a carboxylic acid of general formula I into a salt thereof, or converting a carboxylic acid salt of a compound of general formula I into the free acid or into another salt.

A leaving group is any group that will, under the reaction conditions, cleave from the starting material thus promoting reaction at a specified site.

The leaving group L in a compound of general formula II is conveniently a halogen atom, for example a bromine, chlorine or iodine atom, or, especially, an alkanesulphonyl group, for example methanesulphonyl.

It is preferred that the reaction is carried out under basic conditions. The basic conditions may suitably be provided, for example, by an alkali metal hydride, such as sodium or potassium hydride, an alkaline earth metal hydride, such as calcium hydride, an alkali metal carbonate or bicarbonate, such as sodium or potassium carbonate or sodium bicarbonate, an alkali metal alkoxide, such as potassium t-butoxide, or a tertiary amine, such as triethylamine, pyridine or 1,8-diazabicyclo[5.4.0]-undec-7-ene.

The reaction is suitably carried out in an inert organic solvent such as a hydrocarbon solvent, e.g. benzene or toluene, a chlorinated hydrocarbon, e.g. dichloromethane or chloroform, an alcohol, e.g. methanol or ethanol, an ether, e.g. diethyl ether, tetrahydrofuran, 1,4-dioxane, a ketone, e.g. acetone or methyl ethyl ketone, an ester, e.g. ethyl acetate, an aprotic polar solvent, e.g. dimethylformamide, dimethylacetamide or dimethylsulphoxide or a nitrile, e.g. acetonitrile, or in water, with appropriate selection of the agent generating the basic conditions for the reaction.

The process of the invention may be carried out over a wide temperature range, for example from ambient ($\sim 20°$ C.) to the reflux temperature of the reaction medium.

The amounts of the reactants II and III may vary suitably within the range of 0.1 to 10 moles of II per mole of III. However substantially equimolar amounts of II and III are preferably employed.

The diastereoisomers and enantiomers of the compounds of general formula I may, of course, be prepared using stereo specific starting materials in the process of the present invention, with subsequent separation, for example by chromatography, if appropriate, or, in the case of the enantiomers may be obtained by conventional resolution techniques from a mixture of optical isomers.

The compound of general formula I obtained by the above process may readily be converted to a further compound of general formula I by methods known to a man skilled in the art. Thus for example, a compound of general formula I where $R^1$ and/or $R^2$ represents a halogen atom, suitably chlorine, may be transformed into other derivatives by nucleophilic displacement, for example by reaction with an amine, such as dimethylamine, to give the corresponding compound of general formula I in which $R^1$ and/or $R^2$ represents a substituted amino group. Likewise a compound of general formula I in which $R^1$ and/or $R^2$ represents a halogen atom, may be reacted with an alkylthio organo-metallic compound, for example sodium methanethiolate, to yield the corresponding compound of general formula I in which $R^1$ and/or $R^2$ represents an alkylthio group such as methylthio, or may be hydrogenated to yield the corresponding compound in which $R^1$ and/or $R^2$ is a hydrogen atom. Compounds of general formula I in which COZ represents an ester group may be hydrolysed by methods well known in the art to yield acids of formula I. Alternatively, hydrogenation of, for example, a benzyl ester of formula I can be employed to yield the corresponding acid.

Acid and salt conversion reactions may be carried out using conventional methods as appropriate.

The prepared compounds of general formula I may, if desired, be isolated and purified using conventional techniques.

The starting pyrimidines of general formula II may be prepared by conventional techniques, for example those described in Heterocyclic compounds, 16 "The Pyrimidines" edited by D. J. Brown, Interscience, 1962.

The compounds of general formula III are either known compounds or may be prepared by conventional procedures. Compounds in which X represents an oxygen atom may be prepared, for example, by reducing a corresponding cycloalkanone-2-carboxylate under suitable reducing conditions, for example with sodium borohydride in an inert solvent.

Compounds of the general formula I have been found to have interesting activity as herbicides having a wide range of pre- and post-emergence activity against undesirable species.

The present invention therefore provides a herbicidal composition which comprises a compound of the present invention in association with a carrier.

The present invention additionally encompasses the preparation of such a herbicidal composition by the process of bringing a carrier into association with a compound of the present invention.

Preferably there are at least two carriers in a composition of the present invention, at least one of which is a surface-active agent.

The present invention further provides the use of a compound according to the invention as a herbicide.

Further, in accordance with the invention there is provided a method of combating undesired plant growth at a locus by treating the locus with a composition or compound according to the invention. The locus may, for example, be the soil or plants in a crop area. Application to the locus may be pre-emergence or post-emergence. The dosage of active ingredient used may, for example, be from 0.01 to 10 kg/ha, preferably 0.01 to 4 kg/ha.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ether; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example, the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The herbicidal composition of the invention may also contain other biologically active ingredients, for example compounds possessing herbicidal, insecticidal or fungicidal properties.

The following Examples illustrate the invention. The structures of the compounds of the invention prepared in the following Examples were confirmed by mass spectrometry and NMR. The compounds prepared were in diastereoisomer form and the term cis and trans refer to the steric configuration of the diastereoisomer prepared.

Example 1 cid-Ethyl 2-(4,6-dimethoxypyrimidin-2-yl)oxycyclohexanecarboxylate a) Ethyl cyclohexanone-2-carboxylate (85.0 g, 0.5 mole) was dissolved in ethanol (200 ml) and the solution cooled to 0° C. Sodium borohydride (13.2 g, 0.35 mole) suspended in ethanol (80 ml) was added in small portions whilst the temperature was maintained at below 0° C. After stirring for 2 hours at 0° C. the reaction mixture was made faintly acid by the addition of 50% sulphuric acid and filtered. The filtrate was concentrated in vacuo, taken up in ether and washed with sodium bicarbonate solution. The organic phase was dried over magnesium sulphate and evaporated in vacuo. The residue was chromatographed on silica-gel, eluting initially with 3:1 hexane/ethyl acetate followed by 2:1 hexane/ethyl acetate to give 21.5 g of cis- and 10.0 g of trans-ethyl 2-hydroxycyclohexanecarboxylate.

b) A solution of the cis-hydroxyester prepared in (a) above (1.72 g, 0.01 mole) in dry dimethylformamide (10 ml) was added dropwise to a stirred supension of sodium hydride (0.48 g at a 60% dispersion) in dry dimethyl formamide (20 ml). After stirring for 30 minutes, 4,6-dimethoxy-2-methanesulphonylpyrimidine (2.18 g, 0.01 mole) was added and the reaction mixture stirred and heated to 90° C. for 16 hours. The mixture was concentrated in vacuo, diluted with water and extracted with diethyl ether. The diethyl ether solution was dried over magnesium sulphate and evaporated. The crude product was purified by chromatography on silica-gel, using a 3:1 hexane/ethyl acetate eluant.

Yield = 1.5 g (48%)

Elemental Analysis (%)

Calculated C 58.0 H 7.1 N 9.0

Found C 57.8 H 7.2 N 9.0

Example 2 cis-2-(4,6-Dimethoxypyrimidin-2-yl)oxycyclohexanecarboxylic acid

Sodium hydroxide (0.17 g) in water (20 ml) was added to a stirred solution of the ethyl ester prepared as in Example 1 (1.3 g) in methanol (20 ml). The reaction mixture was stirred at room temperature overnight, concentrated in vacuo and diluted to 100 ml with water. The aqueous solution was washed twice with diethyl ether then acidified with dilute hydrochloric acid. The acidified aqueous mixture was dried over magnesium sulphate and evaporated in vacuo. Trituration of the residue with hexane gave the crude product as a white solid which was recrystallised from water methanol to give a yield of 0.6 g (51%) of the title product having a melting point of 151°–152 ° C.

Elemental Analysis (%)

Calculated C 55.3 H 6.4 N 9.9

Found C 55.3 H 6.5 N 10.1

Examples 3 to 16

Following procedures similar to those described in Examples 1 and 2, further examples of compounds of the invention were prepared, whose chemical analyses and, for those that are solids, melting points are given in Table 1 below. In that Table the compounds are identified by reference to the substituents in the following formula

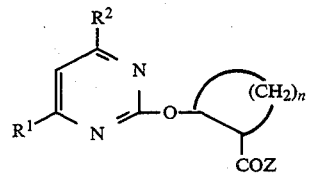

TABLE 1

| Example | $R^1$ | $R^2$ | n | Z | Isomeric Form | Melting Point (°C.) | Analysis (%) C | H | Calc Found N |
|---|---|---|---|---|---|---|---|---|---|
| 3 | $OCH_3$ | $OCH_3$ | 3 | $OC_2H_5$ | mixture | oil | 56.8 | 6.8 | 9.5 |
|   |   |   |   |   |   |   | 56.7 | 6.5 | 9.7 |
| 4 | $OCH_3$ | $OCH_3$ | 3 | $OC_2H_5$ | trans | 30–32 | 56.8 | 6.8 | 9.5 |
|   |   |   |   |   |   |   | 56.2 | 6.7 | 9.8 |
| 5 | $OCH_3$ | $OCH_3$ | 3 | $OC_2H_5$ | cis | oil | 56.8 | 6.8 | 9.5 |
|   |   |   |   |   |   |   | 56.4 | 6.7 | 9.7 |
| 6 | $OCH_3$ | $OCH_3$ | 4 | $OC_2H_5$ | trans | oil | 58.1 | 7.1 | 9.0 |
|   |   |   |   |   |   |   | 58.4 | 7.2 | 9.4 |
| 7 | $OCH_3$ | $OCH_3$ | 5 | $OCH_3$ | trans | oil | 58.0 | 7.1 | 9.0 |
|   |   |   |   |   |   |   | 58.2 | 7.2 | 9.5 |
| 8 | $OCH_3$ | $OCH_3$ | 5 | $OCH_3$ | cis | oil | 58.0 | 7.1 | 9.0 |
| 9 | $OCH_3$ | $OCH_3$ | 4 | $OCH_3$ | cis | 72.5 | 56.8 | 6.8 | 9.5 |
|   |   |   |   |   |   |   | 56.6 | 6.7 | 9.8 |
| 10 | $OCH_3$ | $OCH_3$ | 4 | $OCH_3$ | trans | oil | 56.8 | 6.8 | 9.5 |
|   |   |   |   |   |   |   | 56.1 | 6.7 | 9.6 |
| 11 | $OCH_3$ | $OCH_3$ | 4 | OH | trans | 168.0 | 55.3 | 6.4 | 9.9 |
|   |   |   |   |   |   |   | 55.9 | 6.3 | 9.9 |
| 12 | $CH_3$ | $CH_3$ | 4 | $OCH_3$ | cis | oil | 63.6 | 7.6 | 10.6 |
|   |   |   |   |   |   |   | 63.4 | 7.7 | 10.1 |
| 13 | $CH_3$ | $CH_3$ | 4 | $OCH_3$ | trans | oil | 63.6 | 7.6 | 10.6 |
|   |   |   |   |   |   |   | 63.3 | 7.5 | 10.8 |
| 14 | $OCH_3$ | $OCH_3$ | 3 | $OCH_3$ | trans | oil | 55.3 | 6.4 | 9.9 |
|   |   |   |   |   |   |   | 55.2 | 6.4 | 10.4 |
| 15 | $OCH_3$ | $OCH_3$ | 3 | $OCH_3$ | cis | oil | 55.3 | 6.4 | 9.9 |

TABLE 1-continued

| Example | R¹ | R² | n | Z | Isomeric Form | Melting Point (°C.) | Analysis (%) C | H | Calc Found N |
|---|---|---|---|---|---|---|---|---|---|
| 16 | OCH₃ | OCH₃ | 3 | OH | trans | 113.7 | 56.1 53.7 | 6.4 6.0 | 9.8 10.4 |
| 17 | OCH₃ | OCH₃ | 5 | OH | trans | 103.9 | 53.8 56.8 | 5.9 6.8 | 10.8 9.5 |
| 18 | Cl | OCH₃ | 4 | OC₂H₅ | cis | oil | 57.9 53.4 55.0 | 6.3 6.0 6.2 | 9.3 8.9 8.4 |

Example 19 trans-2-(4,6-Dimethoxypyrimidin-2-yl)oxy-N-benzenesulphonylcyclohexanecarboxamide trans-2-(4,6-Dimethoxypyrimidin-2-yl)oxycyclohexanecarboxylic acid (1.0 g), prepared as in Example 11, in dry tetrahydrofuran (10 ml) was added dropwise to a stirred solution of 1,1-carbonyldiimidazole (0.57 g) in dry tetrahydrofuran (10 ml) under nitrogen. The reaction mixture was stirred 30 minutes at ambient temperature, heated to reflux for 30 minutes and cooled to ambient temperature. Benzenesulphonamide (0.56 g) was added followed by dropwise addition of 1,8-diazabicyclo (5.4.0) undec-7-ene (0.54) in dry tetrahydrofuran (5 ml). The reaction mixture was stirred for 24 hours at ambient temperature, refluxed for 6 hours then poured into 1N hydrochloric acid (80 ml) and extracted with 3×100 ml portions of diethyl ether. The combined ether extracts were dried over magnesium sulphate and evaporated. The residue was chromatographed on silica-gel, using a 2:1 dichloromethane/ethyl acetate eluant, to give 100 mg of the title compound, melting point 175° C.

Element Analysis (%)
Calculated C 54.1 H 5.5 N 10.0
Found C 53.8 H 6.0 N 10.3

Example 20

Herbicidal Activity

To evaluate their herbicidal activity, compounds according to the invention were tested using as representative range of plants: maize, *Zeta mays* (Mz); rice, *Oryza sativa* (R); barnyard grass, *Echinochloa crusgalli* (BG); oat, *Arena sativa* (O); linseed, *Linum usitatissimum* (L); mustard, *Sinapsis alba* (M); sugar beet, *Beta vulgaris* (SB) and soya bean, *Glycine max* (S).

The tests fall into two categories, pre-emergence and post-emergence. The pre-emergence tests involved spraying a liquid formulation of the compound onto the soil in which the seeds of the plant specied mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 600 liters per hectare in the soil spray and foliar spray test, and at a dosage of level equivalent to 10 kilograms of active material per hectare in a volume equivalent to approximately 3,000 liters per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0–9 scale. A rating 0 indicates growth as untreated control, a rating 9 indicates death. An increase of 1 unit on the linear scale approximates to a 10% increase in the level of effect.

The results of the tests are set out in Table II below, in which the compounds are identified by reference to the preceding examples. An asterisk in the Table indicates that no result was obtained.

TABLE II

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 1 | 8 | 8 | 8 | 8 | 7 | 8 | 9 | 7 | 5 | 5 | 8 | 7 | 7 | 7 | 8 | 8 | 8 | 8 | 9 | 8 | 8 | 7 | 7 | 8 | 8 |
| | | | | | | | | | 1 | 4 | 8 | 5 | 7 | 7 | 7 | 8 | 7 | 6 | 9 | 7 | 7 | 6 | 7 | 8 | 4 |
| 2 | 8 | 8 | 8 | 8 | 8 | 8 | 9 | 8 | 5 | 8 | 8 | 9 | 8 | 8 | 8 | 8 | 8 | 8 | 9 | 9 | 8 | 8 | 8 | 8 | 8 |
| | | | | | | | | | 1 | 7 | 8 | 7 | 8 | 7 | 8 | 8 | 7 | 8 | 9 | 9 | 8 | 8 | 8 | 8 | 6 |
| 3 | 7 | 6 | 7 | 7 | 7 | 8 | 8 | 4 | 5 | 7 | 4 | 7 | 6 | 7 | 8 | 7 | 7 | 7 | 9 | 8 | 7 | 6 | 7 | 8 | 4 |
| | | | | | | | | | 1 | 7 | 2 | 5 | 5 | 6 | 8 | 7 | 6 | 4 | 9 | 7 | 4 | 2 | 7 | 7 | 1 |
| 4 | 7 | 7 | 7 | 7 | 7 | 8 | 7 | 6 | 5 | 7 | 5 | 8 | 6 | 7 | 8 | 8 | 8 | 8 | 9 | 9 | 7 | 8 | 7 | 7 | 8 |
| | | | | | | | | | 1 | 7 | 2 | 7 | 4 | 7 | 8 | 8 | 8 | 7 | 9 | 8 | 5 | 7 | 7 | 7 | 7 |
| 5 | 7 | 7 | 7 | 7 | 4 | 8 | 7 | 4 | 5 | 4 | 3 | 4 | 3 | 4 | 7 | 5 | 5 | 3 | 8 | 5 | 4 | 0 | 5 | 3 | 0 |
| | | | | | | | | | 1 | * | * | * | * | * | * | * | * | * | * | * | * | * | * | * | * |
| 6 | 8 | 8 | 8 | 8 | 7 | 9 | 9 | 8 | 5 | 7 | 8 | 8 | 8 | 7 | 9 | 9 | 8 | 9 | 9 | 9 | 8 | 9 | 7 | 8 | 8 |
| | | | | | | | | | 1 | 7 | 8 | 8 | 8 | 7 | 8 | 8 | 8 | 8 | 9 | 9 | 8 | 7 | 7 | 8 | 8 |
| 7 | 7 | 7 | 8 | 7 | 7 | 7 | 8 | 7 | 5 | 7 | 6 | 8 | 7 | 7 | 8 | 8 | 7 | 9 | 9 | 9 | 8 | 8 | 7 | 8 | 8 |
| 8 | 7 | 7 | 7 | 7 | 6 | 6 | 7 | 6 | 5 | 6 | 6 | 8 | 6 | 7 | 7 | 8 | 6 | 7 | 8 | 8 | 7 | 7 | 6 | 8 | 2 |
| | | | | | | | | | 1 | 2 | 5 | 3 | 5 | 6 | 4 | 5 | 4 | 5 | 7 | 7 | 6 | 5 | 5 | 6 | 0 |

TABLE II-continued

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 9 | 7 | 7 | 7 | 7 | 7 | 7 | 8 | 7 | 5 | 7 | 7 | 7 | 7 | 7 | 7 | 8 | 7 | 8 | 9 | 9 | 8 | 8 | 7 | 8 | 8 |
| | | | | | | | | | 1 | 6 | 7 | 5 | 7 | 6 | 5 | 7 | 7 | 7 | 9 | 8 | 7 | 7 | 6 | 8 | 8 |
| 10 | 8 | 8 | 9 | 9 | 8 | 8 | 8 | 8 | 5 | 8 | 8 | 9 | 8 | 8 | 9 | 8 | 8 | 9 | 9 | 9 | 8 | 9 | 8 | 8 | 8 |
| | | | | | | | | | 1 | 8 | 8 | 8 | 8 | 8 | 8 | 8 | 8 | 9 | 9 | 9 | 8 | 8 | 8 | 8 | 8 |
| 11 | 9 | 9 | 9 | 8 | 8 | 9 | 9 | 8 | 5 | 9 | 9 | 9 | 9 | 8 | 9 | 8 | 8 | 9 | 9 | 9 | 9 | 9 | 8 | 8 | 8 |
| | | | | | | | | | 1 | 8 | 8 | 9 | 8 | 8 | 8 | 8 | 8 | 9 | 9 | 9 | 8 | 9 | 8 | 8 | 8 |
| 12 | 7 | 7 | 7 | 6 | 3 | 6 | 8 | 3 | 5 | 6 | 6 | 7 | 7 | 0 | 2 | 3 | 2 | 7 | 8 | 9 | 7 | 2 | 0 | 5 | 0 |
| | | | | | | | | | 1 | 2 | 6 | 7 | 5 | 0 | 2 | 0 | 0 | 4 | 7 | 8 | 6 | 0 | 0 | 3 | 0 |
| 13 | 7 | 7 | 8 | 6 | 0 | 3 | 7 | 2 | 5 | 2 | 6 | 7 | 4 | 0 | 4 | 4 | 0 | 5 | * | 7 | 6 | 2 | 2 | 2 | 0 |
| | | | | | | | | | 1 | 0 | 5 | 4 | 2 | 0 | 1 | 1 | 0 | 1 | 4 | 5 | 3 | 0 | 0 | 0 | 0 |
| 14 | 7 | 7 | 8 | 6 | 7 | 7 | 8 | 5 | 5 | 7 | 7 | 7 | 3 | 7 | 8 | 9 | 8 | 8 | * | 8 | 4 | 7 | 7 | 8 | 4 |
| | | | | | | | | | 1 | 6 | 6 | 6 | 2 | 6 | 7 | 8 | 5 | 4 | 8 | 8 | 1 | 5 | 6 | 7 | 3 |
| 15 | 7 | 7 | 7 | 6 | 4 | 7 | 9 | 2 | 5 | 4 | 7 | 5 | 2 | 5 | 7 | 9 | 3 | 4 | 7 | 8 | 6 | 4 | 7 | 5 | 0 |
| | | | | | | | | | 1 | 1 | 6 | 3 | 0 | 3 | 6 | 6 | 1 | 1 | 5 | 6 | 2 | 1 | 5 | 3 | 0 |
| 16 | 7 | 8 | 8 | 5 | 8 | 8 | 8 | 5 | 5 | 7 | 7 | 8 | 6 | 8 | 8 | 8 | 8 | 8 | 9 | 8 | 6 | 7 | 7 | 8 | 8 |
| | | | | | | | | | 1 | 7 | 7 | 8 | 6 | 7 | 8 | 7 | 8 | 7 | 9 | 8 | 3 | 5 | 6 | 7 | 2 |
| 17 | 7 | 8 | 8 | 7 | 6 | 8 | 9 | 7 | 5 | 7 | 7 | 8 | 7 | 6 | 7 | 8 | 7 | 8 | 9 | 8 | 6 | 7 | 6 | 8 | 3 |
| | | | | | | | | | 1 | * | * | * | * | * | * | * | * | * | * | * | * | * | * | * | * |
| 18 | 8 | 8 | 7 | 8 | 4 | 7 | 8 | 8 | 5 | 5 | 7 | 7 | 7 | 7 | 7 | 8 | 6 | 8 | 9 | 9 | 8 | 8 | 8 | 8 | 4 |
| | | | | | | | | | 1 | 3 | 6 | 4 | 6 | 6 | 6 | 8 | 4 | 4 | 8 | 9 | 7 | 7 | 6 | 8 | 3 |
| 19 | * | * | * | * | * | * | * | * | 5 | 0 | 5 | 7 | 4 | 6 | 7 | 4 | 5 | 2 | 5 | 7 | 6 | 5 | 6 | 6 | 3 |
| | | | | | | | | | 1 | * | * | * | * | * | * | * | * | * | * | * | * | * | * | * | * |

Example 21

Herbicidal Selectivity

To evaluate their herbicidal selectivity, compounds according to the invention were spray tested using as a representative range of plants the following seedling test plant species: wheat, *triticum aestivm* (WH); barley, *hordeum vulgare* (BA); blackgrass, *alopecurus myosuroides* (AM); wild oat, *avena fatua* (WO); couchgrass, *elymus repens* (CO); meadow grass (annual), *poa annua* (PA); spurry, *spergula arvensis* (SY); sugar beet, *beta vulgaris* (SB); oil-seed rape, *brassica napus* (RA); cleavers, *galium aparine* (GG); chickweed, *stellaria media* (ST); field pansy, *viola arvensis* (FP); and pale persicaria, *polygonum lapathifolium* (PP).

The results were subjected to a standard probit analysis by computer to calculate the dosage of each compound in g/ha required to kill 50% of the weed species and to produce 50% level of effect on the crop species. These dosages are referred to as the $GID_{50}$ value.

The $GID_{50}$ values for compounds of the invention are set out below in Table III. These $GID_{50}$ values were then used to calculate the selectivity factors in wheat by dividing the $GID_{50}$ value of the compounds in wheat by their $GID_{50}$ value in each weed species. The results are set out in Table IV. (Numbers greater than 1 indicate selectivity between crop and weed and the larger the number the greater the selectivity).

TABLE III

| Ex. | WH | BA | AM | WO | CO | PA | SY | SB | RA | GG | ST | FP | PP |
|---|---|---|---|---|---|---|---|---|---|---|---|---|---|
| 1 | 0.44 | 0.09 | 0.07 | 0.09 | 0.03 | 0.19 | — | 0.06 | 0.79 | 0.08 | 0.13 | <0.02 | 0.07 |
| 4 | >2.00 | 0.59 | 0.69 | 2.00 | 0.81 | 1.32 | 0.09 | 0.14 | <0.02 | 0.07 | 0.03 | <0.02 | 0.07 |
| 6 | 0.06 | 0.02 | <0.02 | 0.03 | <0.02 | 0.03 | — | <0.02 | 0.14 | 0.02 | <0.02 | <0.02 | <0.02 |
| 7 | 0.55 | 0.06 | 0.04 | 0.09 | 0.02 | 0.23 | — | 0.02 | 0.06 | 0.03 | 0.03 | 0.03 | 0.02 |
| 8 | >2.00 | — | 0.47 | — | — | — | — | 0.37 | 1.64 | 1.43 | — | — | — |
| 9 | >2.00 | 0.17 | 0.07 | 0.11 | 0.03 | 0.18 | — | 0.03 | 1.58 | 0.10 | 0.40 | 0.06 | 0.19 |
| 10 | 0.09 | 0.02 | <0.02 | 0.03 | <0.02 | 0.04 | — | <0.02 | 0.20 | <0.02 | <0.02 | <0.02 | <0.02 |
| 12 | >2.00 | — | 0.10 | — | — | — | — | 1.10 | >2.00 | >2.00 | — | — | — |
| 13 | >2.00 | — | 0.93 | — | — | — | — | 0.93 | 1.64 | >2.00 | — | — | — |
| 14 | 0.98 | 0.18 | 0.10 | >2.00 | 0.04 | 0.44 | — | 0.23 | <0.02 | 0.17 | <0.02 | — | 0.13 |
| 16 | 1.30 | 0.23 | 0.11 | 1.13 | 0.23 | 0.29 | 0.02 | 0.07 | <0.02 | 0.04 | <0.02 | <0.02 | 0.03 |
| 17 | 0.27 | — | 0.03 | — | — | — | — | 0.07 | 0.81 | 0.19 | — | — | — |
| 18 | 1.25 | 0.37 | 0.08 | 0.47 | 1.56 | — | — | 0.07 | 0.07 | 0.06 | 0.41 | 0.07 | 0.67 |
| 19 | >2.00 | — | 0.75 | — | — | — | — | 0.91 | 0.02 | 0.75 | — | — | — |

TABLE IV

| Ex. | BA | AM | WO | CO | PA | SY | SB | RA | GG | ST | FP | PP |
|---|---|---|---|---|---|---|---|---|---|---|---|---|
| 1 | 4.9 | 6.3 | 4.9 | 14.7 | 2.3 | — | 7.3 | 0.6 | 5.5 | 3.4 | >22.0 | 6.3 |
| 4 | >3.4 | >2.9 | >1.0 | >2.5 | >1.5 | >22.2 | >14.3 | >100.0 | >28.6 | >66.7 | >100.0 | >28.6 |
| 6 | 3.0 | >3.0 | 2.0 | >3.0 | 2.0 | — | 3.0 | 0.4 | 3.0 | >3.0 | >3.0 | >3.0 |
| 7 | 9.2 | 13.8 | 6.1 | 27.5 | 2.4 | — | 27.5 | 9.2 | 18.3 | 18.3 | 18.3 | 27.5 |
| 8 | — | >4.3 | — | — | — | — | >5.4 | >1.2 | >1.4 | — | — | — |
| 9 | >11.8 | >28.6 | >18.2 | >66.7 | >11.1 | — | >66.7 | >1.3 | >20.0 | >5.0 | >33.3 | >10.5 |
| 10 | 4.5 | >4.5 | 3.0 | >4.5 | 2.3 | — | >4.5 | 0.5 | >4.5 | >4.5 | >4.5 | >4.5 |
| 12 | — | >20.0 | — | — | — | — | >1.8 | 1.0 | 1.0 | — | — | — |
| 13 | — | >2.2 | — | — | — | — | >2.2 | >1.2 | 1.0 | — | — | — |
| 14 | 5.4 | 9.8 | <0.5 | 24.5 | 2.2 | — | 4.3 | >49.0 | 5.8 | >49.0 | — | 7.5 |
| 16 | 5.7 | 11.8 | 1.2 | 5.7 | 4.5 | 65.0 | 18.6 | >65.0 | 32.5 | >65.0 | >65.0 | 43.3 |
| 17 | — | 9.0 | — | — | — | — | 3.9 | 0.3 | 1.4 | — | — | — |

TABLE IV-continued

| Ex. | BA | AM | WO | CO | PA | SY | SB | RA | GG | ST | FP | PP |
|---|---|---|---|---|---|---|---|---|---|---|---|---|
| 18 | 3.4 | 15.6 | 2.7 | 0.8 | — | — | 17.9 | 17.9 | 20.8 | 3.0 | 17.9 | 1.9 |
| 19 | — | >2.7 | — | — | — | — | >2.2 | >100.0 | >2.7 | — | — | — |

The data of Table III demonstrates that the compounds of the present invention exhibit a general selectivity toward the treatment of wheat in comparison to the other of the tested plant species as evidenced by the higher $GID_{50}$ values for wheat. That is, undesirable plant growth may be treated with the compounds of the present invention in the presence of wheat in order to eradicate the undesirable plant species while minimizing adverse effects to the wheat itself due to the fact that the wheat exhibits greater resistance to treatment with the compounds of the present invention. The data of Table IV further confirms that the non-wheat plant species are more susceptible to treatment with the compounds of the present invention in comparison to wheat.

We claim:

1. A method of combating undesired plant growth in wheat, comprising treating said undesired plant growth with an effective amount of a compound of the formula I

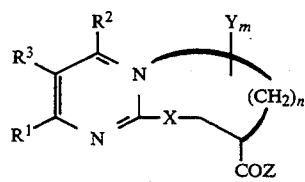

in which
n is an integer from 1 to 6;
m is an integer from 0 to $2n+2$;
X represents an oxygen or sulphur atom or a sulphinyl or sulphonyl group;
$R^1$, $R^2$ and $R^3$ each independently represents a hydrogen or halogen atom, a formyl, cyano, carboxy or azido group, or an optionally substituted $C_{1-12}$ alkyl, $C_{2-12}$ alkenyl, $C_{2-12}$ alkynyl, $C_{1-12}$ alkoxy, $C_{2-12}$ alkenyloxy, $C_{2-12}$ alkynyloxy, $C_{1-12}$ alkylthio, $C_{2-12}$ alkenylthio, $C_{2-12}$ alkynylthio, $C_{1-12}$ alkylcarbonyl, $C_{1-12}$ alkoxycarbonyl, amino, aminoxy or di-$C_{1-12}$ alkyliminoxy group;
Z represents a hydrogen or halogen atom, ($C_{3-8}$ cycloalkyl)oxy, $C_{1-12}$ alkylthio, $C_{2-12}$ alkenylthio, $C_{2-12}$ alkynylthio, phenylthio, sulphonamido, aminoxy or di-$C_{1-12}$ alkyliminoxy group; and
Y represents a halogen atom, a cyano or carboxy group, or an optionally substituted $C_{1-12}$ alkyl, $C_{2-12}$ alkenyl, $C_{2-12}$ alkynyl, $C_{1-12}$ alkoxy, $C_{2-12}$ alkenyloxy, $C_{2-12}$ alkynyloxy, $C_{1-12}$ alkylthio, $C_{2-12}$ alkenylthio, $C_{2-12}$ alkynylthio, phenyloxy, $C_{1-12}$ alkylcarbonyl or $C_{1-12}$ alkoxycarbonyl group;
said optional substituents for $C_{1-12}$ alkyl, $C_{2-12}$ alkenyl, $C_{2-12}$ alkynyl, $C_{1-12}$ alkoxy, $C_{2-12}$ alkenyloxy, $C_{2-12}$ alkynyloxy, $C_{1-12}$ alkylthio, $C_{2-12}$ alkenylthio, $C_{2-12}$ alkynylthio, $C_{1-12}$ alkylcarbonyl, $C_{1-12}$ alkoxycarbonyl or cycloalkoxy groups being independently selected from one or more of halogen atoms and $C_{1-12}$ alkoxy, $C_{2-12}$ alkenyloxy, hydroxy, $C_{1-12}$ alkylthio, $C_{1-12}$ alkylsulphonyl, $C_{1-12}$ alkylsulphinyl, $C_{1-12}$ alkylenedioxy, $C_{1-12}$ alkylenedithio, halo $C_{1-12}$ alkyl and $C_{1-12}$ alkoxycarbonyl groups, and di-$C_{1-12}$ alkyliminoxy, optionally substituted amino, tri-$C_{1-12}$ alkylsilyl, $C_{1-12}$ alkylcarbonyl, $C_{1-12}$ alkoxycarbonyl, carboxy, cyano, thiocyanato and optional substituted aminocarbonyl groups,
said optional substituents for Z being independently selected from phenyl, phenyloxy, phenylthio, and phenylcarbonyl,
said optional substituents for phenyl, phenyloxy or phenylthio groups being independently selected from one or more of halogen atoms and nitro, cyano, $C_{1-12}$ alkyl, halo $C_{1-12}$ alkyl, $C_{1-12}$ alkoxy, $C_{1-12}$ alkylthio, phenyloxy, $C_{1-12}$ alkoxycarbonyl and aralkoxycarbonyl groups,
said optional substituents for an amino group or for an amino moiety in an aminoxy or aminocarbonyl group, being independently selected from $C_{1-12}$ alkyl, $C_{2-12}$ alkenyl, phenyl, $C_{1-12}$ alkoxy, amino, mono- or di-$C_{1-12}$ alkylamino, phenylamine, $C_{1-12}$ alkoxyalkyl, halo $C_{1-12}$ alkyl, hydroxy, hydroxy $C_{1-12}$ alkyl, cyano, carboxy $C_{1-12}$ alkyl or $C_{1-12}$ alkylcarbonylamino,
said optional substituents for a sulphonamido group being optionally substituted $C_{1-12}$ alkyl or phenyl, optionally in association with a carrier.

2. A method as claimed in claim 1, in which $R^1$ and $R^2$ each independently represents a halogen atom, a $C_{1-4}$alkyl group, a $C_{1-4}$alkoxy group, a $C_{1-4}$alkylthio group or a mono- or di-$C_{1-4}$alkylamino group, and $R^3$ represents a hydrogen atom.

3. A method as claimed in claim 2, in which $R^1$ and $R^2$ each independently represents a chlorine atom, a methyl group or a methoxy group.

4. A method as claimed in claim 1, in which n is 3, 4 or 5.

5. A compound as claimed in claim 1, in which X represents an oxygen atom.

6. A method as claimed in claim 1, wherein Y represents a halogen, carboxy or cyano group, or an optionally substituted $C_{2-12}$ alkenyl, $C_{2-12}$ alkynyl, $C_{2-12}$ alkoxy, $C_{2-12}$ alkenyloxy, $C_{2-12}$ alkynyloxy, $C_{1-12}$ alkylthio, $C_{2-12}$ alkenylthio, $C_{2-12}$ alkynylthio, phenyloxy, or $C_{1-12}$ alkylcarbonyl group.

7. A method as claimed in claim 1, wherein Z represents hydrogen, halogen, or optionally substituted $C_{1-12}$ alkylthio, $C_{2-12}$ alkenylthio, $C_{2-12}$ alkynylthio, phenylthio, sulphonamido, aminoxy, or di-$C_{1-12}$ alkyliminoxy.

8. A method as claimed in claim 1 wherein said undesired plant growth is treated with said compound in association with a carrier for said compound.

9. A method as claimed in claim 1 wherein said undesired plant growth is selected from the group consisting of *hordeum vulgare, alopecurus myosuroides, arena fatua, elymus repens, poa annua, spergula arvensis, beta vulgaris, brassica napus, galium aparine, stellaria media, viola arvensis,* and *polygonum lapathifolium.*

10. A method as claimed in claim 1 wherein $R^1$ and $R^2$ each independently represents $C_{1-12}$ alkyl or $C_{1-12}$ alkoxy, X represents oxygen, m is 0, $R^3$ is hydrogen and n is an integer from 3 to 5.

11. A method of combating undesired plant growth in wheat, comprising treating said undesired plant growth with an effective amount of a compound of the formula I

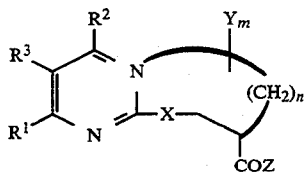

in which
n is an integer from 1 to 6;
m is an integer from 0 to $2n+2$;
X represents an oxygen or sulphur atom or a sulphinyl or sulphonyl group;
$R^1$, $R^2$ and $R^3$ each independently represents a hydrogen or halogen atom, a formyl, cyano, carboxy or azido group, or an optionally substituted $C_{1-12}$ alkyl, $C_{2-12}$ alkenyl, $C_{2-12}$ alkynyl, $C_{1-12}$ alkoxy, $C_{2-12}$ alkenyloxy, $C_{2-12}$ alkynyloxy, $C_{1-12}$ alkylthio, $C_{2-12}$ alkenylthio, $C_{2-12}$ alkynylthio, $C_{1-12}$ alkylcarbonyl, $C_{1-12}$ alkoxycarbonyl, amino, aminoxy or di-$C_{1-12}$ alkyliminoxy group;
Z represents a hydrogen or halogen atom, a hydroxy group, an optionally substituted $C_{1-12}$ alkoxy, $C_{2-12}$ alkenyloxy, $C_{2-12}$ alkynyloxy, ($C_{3-8}$ cycloalkyl)oxy, phenyloxy, $C_{1-12}$ alkylthio, $C_{2-12}$ alkenylthio, $C_{2-12}$ alkynylthio, phenylthio, sulphonamido, aminoxy or di-$C_{1-12}$ alkyliminoxy group; and
Y represents a halogen atom, a cyano or carboxy group, or an optionally substituted $C_{1-12}$ alkyl, $C_{2-12}$ alkenyl, $C_{2-12}$ alkynyl, $C_{1-12}$ alkoxy, $C_{2-12}$ alkenyloxy, $C_{2-12}$ alkynyloxy, $C_{1-12}$ alkylthio, $C_{2-12}$ alkenylthio, $C_{2-12}$ alkynylthio, phenyloxy, $C_{1-12}$ alkylcarbonyl or $C_{1-12}$ alkoxycarbonyl group;
or a carboxylic acid salt of a compound of formula I with an equivalent amount of an inorganic or organic cation,
said optional substituents for $C_{1-12}$ alkyl, $C_{2-12}$ alkenyl, $C_{2-12}$ alkynyl, $C_{1-12}$ alkoxy, $C_{2-12}$ alkenyloxy, $C_{2-12}$ alkynyloxy, $C_{1-12}$ alkylthio, $C_{2-12}$ alkenylthio, $C_{2-12}$ alkynylthio, $C_{1-12}$ alkylcarbonyl, $C_{1-12}$ alkoxycarbonyl or cycloalkoxy groups being independently selected from one or more of halogen atoms and $C_{1-12}$ alkoxy, $C_{2-12}$ alkenyloxy, hydroxy, $C_{1-12}$ alkylthio, $C_{1-12}$ alkylsulphonyl, $C_{1-12}$ alkylsulphinyl, $C_{1-12}$ alkylenedioxy, $C_{1-12}$ alkylenedithio, halo $C_{1-12}$ alkyl and $C_{1-12}$ alkoxycarbonyl groups, and di-$C_{1-12}$ alkyliminoxy, optionally substituted amino, tri-$C_{1-12}$ alkylsilyl, $C_{1-12}$ alkylcarbonyl, $C_{1-12}$ alkoxycarbonyl, carboxy, cyano, thiocyanato and optional substituted aminocarbonyl groups,
said optional substituents for Z being independently selected from phenyl, phenyloxy, phenylthio and phenylcarbonyl,
said optional substituents for phenyl, phenyloxy or phenylthio groups being independently selected from one or more of halogen atoms and nitro, cyano, $C_{1-12}$ alkyl, halo $C_{1-12}$ alkyl, $C_{1-12}$ alkoxy, $C_{1-12}$ alkylthio, phenyloxy, $C_{1-12}$ alkoxycarbonyl and aralkoxycarbonyl groups,
said optional substituents for an amino group or for an amino moiety in an aminoxy or aminocarbonyl group, being independently selected from $C_{1-12}$ alkyl, $C_{2-12}$ alkenyl, phenyl, $C_{1-12}$ alkoxy, amino, mono- or di-$C_{1-12}$ alkylamino, phenylamine, $C_{1-12}$ alkoxyalkyl, halo $C_{1-12}$ alkyl, hydroxy, hydroxy $C_{1-12}$ alkyl, cyano, carboxy $C_{1-12}$ alkyl or $C_{1-12}$ alkylcarbonylamino,
said optional substituents for a sulphonamido group being optionally substituted $C_{1-12}$ alkyl or phenyl,
optionally in association with a carrier,
and wherein said undesired plant growth is selected from the group consisting of *hordeum vulgare, alopecurus myosuroides, avena fatua, elymus repens, poa annua, spergula arvensis, beta vulgaris, brassica napus, galium aparine, stellaria media, viola arvensis,* and *polygonum lapathifolium.*

12. A method as claimed in claim 11, in which $R^1$ and $R^2$ each independently represents a halogen atom, a $C_{1-4}$ alkyl group, a $C_{1-4}$ alkoxy group, a $C_{1-4}$ alkylthio group or a mono- or di-$C_{1-4}$ alkylamino group, and $R^3$ represents a hydrogen atom.

13. A method as claimed in claim 12, in which $R^1$ and $R^2$ each independently represents a chlorine atom, a methyl group or a methoxy group.

14. A method as claimed in claim 11, in which n is 3, 4 or 5.

15. A method as claimed in claim 11, in which the substituent group COZ represents a carboxy group, a ($C_{1-4}$ alkoxy)carbonyl group or a phenyl-sulphonylcarbamoyl group.

16. A method as claimed in claim 11, in which X represents an oxygen atom.

17. A method as claimed in claim 11, wherein Y represents a halogen, carboxy or cyano group, or an optionally substituted $C_{2-12}$ alkenyl, $C_{2-12}$ alkynyl, $C_{2-12}$ alkoxy, $C_{2-12}$ alkenyloxy, $C_{2-12}$ alkynyloxy, $C_{1-12}$ alkylthio, $C_{2-12}$ alkenylthio, $C_{2-12}$ alkynylthio, phenyloxy, or $C_{1-12}$ alkylcarbonyl group.

18. A method as claimed in claim 11, wherein Z represents hydrogen, halogen, or optionally substituted $C_{1-12}$ alkylthio, $C_{2-12}$ alkenylthio, $C_{2-12}$ alkynylthio, phenylthio, sulphonamido, aminoxy, or di-$C_{1-12}$ alkyliminoxy.

19. A method as claimed in claim 11 wherein said undesired plant growth is treated with said compound in association with a carrier for said compound.

20. A method as claimed in claim 11, wherein $R^1$ and $R^2$ each independently represents $C_{1-12}$ alkyl or $C_{1-12}$ alkoxy, X represents oxygen, m is 0 and $R^3$ is hydrogen and n is an integer from 3 to 5.

* * * * *

UNITED STATES PATENT AND TRADEMARK OFFICE
CERTIFICATE OF CORRECTION

PATENT NO.   : 5,426,090
DATED        : June 20, 1995
INVENTOR(S)  : ALASTAIR MCARTHUR ET AL.

It is certified that error appears in the above-indentified patent and that said Letters Patent is hereby corrected as shown below:

On the cover page, in the abstract;

In the claims, column 13, claim 1 and column 15, claim 11;
Formula I should read as follows:

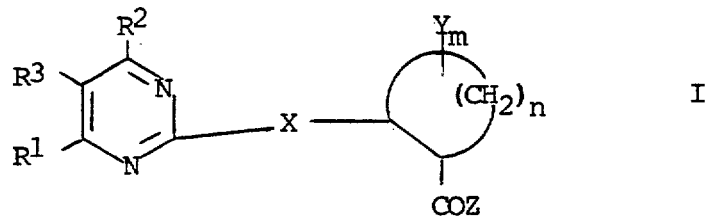

UNITED STATES PATENT AND TRADEMARK OFFICE
CERTIFICATE OF CORRECTION

PATENT NO. : 5,426,090
DATED : June 20, 1995
INVENTOR(S) : ALASTAIR MCARTHUR ET AL.

It is certified that error appears in the above-indentified patent and that said Letters Patent is hereby corrected as shown below:

column 4, Formula III should read as follows:

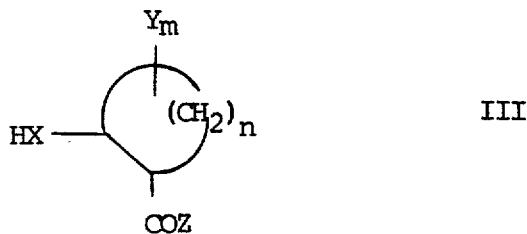

Claim 9, column 14, line 3, "arena" should read --avena--.

UNITED STATES PATENT AND TRADEMARK OFFICE
CERTIFICATE OF CORRECTION

PATENT NO.   : 5,426,090
DATED        : June 20, 1995
INVENTOR(S)  : ALASTAIR MCARTHUR ET AL.

It is certified that error appears in the above-indentified patent and that said Letters Patent is hereby corrected as shown below:

column 3, Formula (Ia) should read as follows:

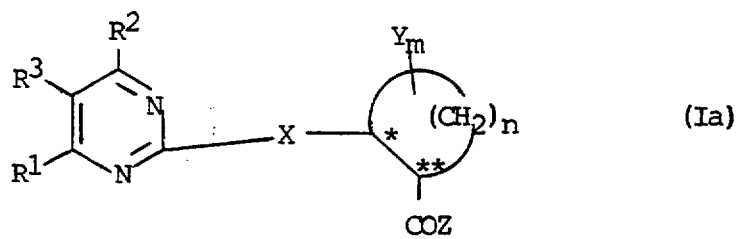

Signed and Sealed this

Twenty-ninth Day of August, 1995

Attest:

BRUCE LEHMAN

Attesting Officer    Commissioner of Patents and Trademarks